(12) United States Patent  
Sharma et al.

(10) Patent No.: US 11,617,508 B2  
(45) Date of Patent: Apr. 4, 2023

(54) EYE-TRACKING FUNDUS IMAGING SYSTEM

(71) Applicant: Meta Platforms Technologies, LLC, Menlo Park, CA (US)

(72) Inventors: Robin Sharma, Redmond, WA (US); Mohamed Tarek El-Haddad, Redmond, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 31 days.

(21) Appl. No.: 16/844,877

(22) Filed: Apr. 9, 2020

(65) Prior Publication Data

US 2021/0267450 A1 Sep. 2, 2021

Related U.S. Application Data

(60) Provisional application No. 62/983,339, filed on Feb. 28, 2020.

(51) Int. Cl.
*G02B 27/00* (2006.01)  
*A61B 3/12* (2006.01)  
(Continued)

(52) U.S. Cl.  
CPC ............... *A61B 3/12* (2013.01); *A61B 3/005* (2013.01); *A61B 3/0025* (2013.01); *A61B 3/113* (2013.01);  
(Continued)

(58) Field of Classification Search  
CPC ......... A61B 3/12; A61B 3/0025; A61B 3/005; A61B 3/113; A61B 3/14; A61B 2090/502; H04N 5/2254; H04N 5/2354  
See application file for complete search history.

(56) References Cited

U.S. PATENT DOCUMENTS

| | | | |
|---|---|---|---|
| 5,815,741 A | 9/1998 | Okuyama et al. | |
| 6,027,216 A * | 2/2000 | Guyton | A61B 3/113 351/200 |
| 8,596,786 B2 | 12/2013 | Bublitz et al. | |
| 10,268,268 B1 | 4/2019 | Trail | |

(Continued)

FOREIGN PATENT DOCUMENTS

| | | |
|---|---|---|
| EP | 3079560 A1 | 10/2016 |
| WO | 2016162822 A1 | 10/2016 |

OTHER PUBLICATIONS

International Searching Authority, Patent Cooperation Treaty, European Application No. PCT/US2021/014970, dated Apr. 15, 2021, 3 pages.

(Continued)

*Primary Examiner* — Patrick E Demosky  
(74) *Attorney, Agent, or Firm* — Freestone Intellectual Property Law PLLC; Aaron J. Visbeek; Andrew J. Cameron

(57) ABSTRACT

A fundus illumination system includes an array of light sources, a first optical combiner, and a second optical combiner. The array of light sources are configured to be selectively enabled to emit non-visible light to illuminate a fundus of an eye. The first optical combiner is configured to receive reflected non-visible light that is reflected by the eye, direct a first component of the reflected non-visible light to a first camera to generate an image of the eye, and pass a second component of the reflected non-visible light. The second optical combiner is configured to receive a fundus imaging light responsive to the second component of the reflected non-visible light, and to direct the fundus imaging light to a second camera to generate an image of the fundus.

19 Claims, 6 Drawing Sheets

(51) Int. Cl.
*H04N 5/225* (2006.01)
*H04N 5/235* (2006.01)
*A61B 3/113* (2006.01)
*A61B 3/00* (2006.01)
*A61B 3/14* (2006.01)
*A61B 90/50* (2016.01)

(52) U.S. Cl.
CPC .............. *A61B 3/14* (2013.01); *H04N 5/2254* (2013.01); *H04N 5/2354* (2013.01); *A61B 2090/502* (2016.02)

(56) References Cited

U.S. PATENT DOCUMENTS

| | | | |
|---|---|---|---|
| 10,274,730 B2 | 4/2019 | Jepsen et al. | |
| 2008/0100803 A1* | 5/2008 | Dick | A61B 3/14 351/212 |
| 2018/0070819 A1 | 3/2018 | Kanamori et al. | |
| 2018/0129167 A1 | 5/2018 | Maimone et al. | |
| 2019/0019023 A1 | 1/2019 | Konttori et al. | |
| 2019/0046031 A1 | 2/2019 | Kramer et al. | |
| 2019/0101767 A1 | 4/2019 | Geng et al. | |
| 2019/0282089 A1 | 9/2019 | Wang | |
| 2019/0361250 A1 | 11/2019 | Lanman et al. | |
| 2021/0165207 A1* | 6/2021 | Peyman | A61F 2/1635 |

OTHER PUBLICATIONS

International Searching Authority, Patent Cooperation Treaty, Written Opinion of the International Searching Authority, European Application No. PCT/US2021/014970, dated Apr. 15, 2021, 5 pages.
International Searching Authority, Patent Cooperation Treaty, European Application No. PCT/US2021/019912, dated Jun. 18, 2021, 9 pages.
Final Office Action dated Jul. 19, 2022 for U.S. Appl. No. 16/844,890, filed Apr. 9, 2020, 14 pages.
International Preliminary Report on Patentability for International Application No. PCT/US2020/063513, dated Aug. 18, 2022, 8 pages.
International Preliminary Report on Patentability for International Application No. PCT/US2021/019912, dated Sep. 9, 2022, 8 pages.
International Searching Authority, Patent Cooperation Treaty, Written Opinion of the International Searching Authority, European Application No. PCT/US2020/063513, dated Feb. 18, 2021, 9 pages.
International Searching Authority, Patent Cooperation Treaty, Written Opinion of the International Searching Authority, European Application No. PCT/US2021/014693, dated Mar. 12, 2021, 12 pages.

* cited by examiner

EYE-TRACKING FUNDUS IMAGING SYSTEM

CROSS-REFERENCE TO RELATED APPLICATION

The present Application claims the benefit of U.S. Provisional Application No. 62/983,339, entitled "Eye-Tracking Fundus Imaging System" filed Feb. 28, 2020. U.S. Provisional Application No. 62/983,339 is expressly incorporated herein by reference in their entirety.

FIELD OF DISCLOSURE

Aspects of the present disclosure relate generally to ocular fundus illumination and imaging systems.

BACKGROUND

Fundus imaging involves imaging (e.g., photographing) the rear portion of the eye, also referred to as the fundus. In particular, the fundus of the eye is the interior surface of the eye, opposite the lens, and may include the retina, optic disc, macula, fovea, and posterior pole. In some contexts, analysis of fundus images may be useful by a care provider for diagnostic or treatment response purposes. For example, a physician may be able to identify issues, such as infections, degenerative eye diseases, or even congenital conditions based on the examination of the fundus images.

Some conventional fundus imaging systems may include various optics and a flash enabled camera. The operation of these conventional imaging systems may include directing a patient to fixate on a target image (e.g., a dot) that is projected onto the retina, and then flooding the pupil with light (e.g., activate the flash) to obtain the image.

BRIEF DESCRIPTION OF THE DRAWINGS

Non-limiting and non-exhaustive aspects of the present disclosure are described with reference to the following figures, wherein like reference numerals refer to like parts throughout the various views unless otherwise specified.

DETAILED DESCRIPTION

Figure 1A:
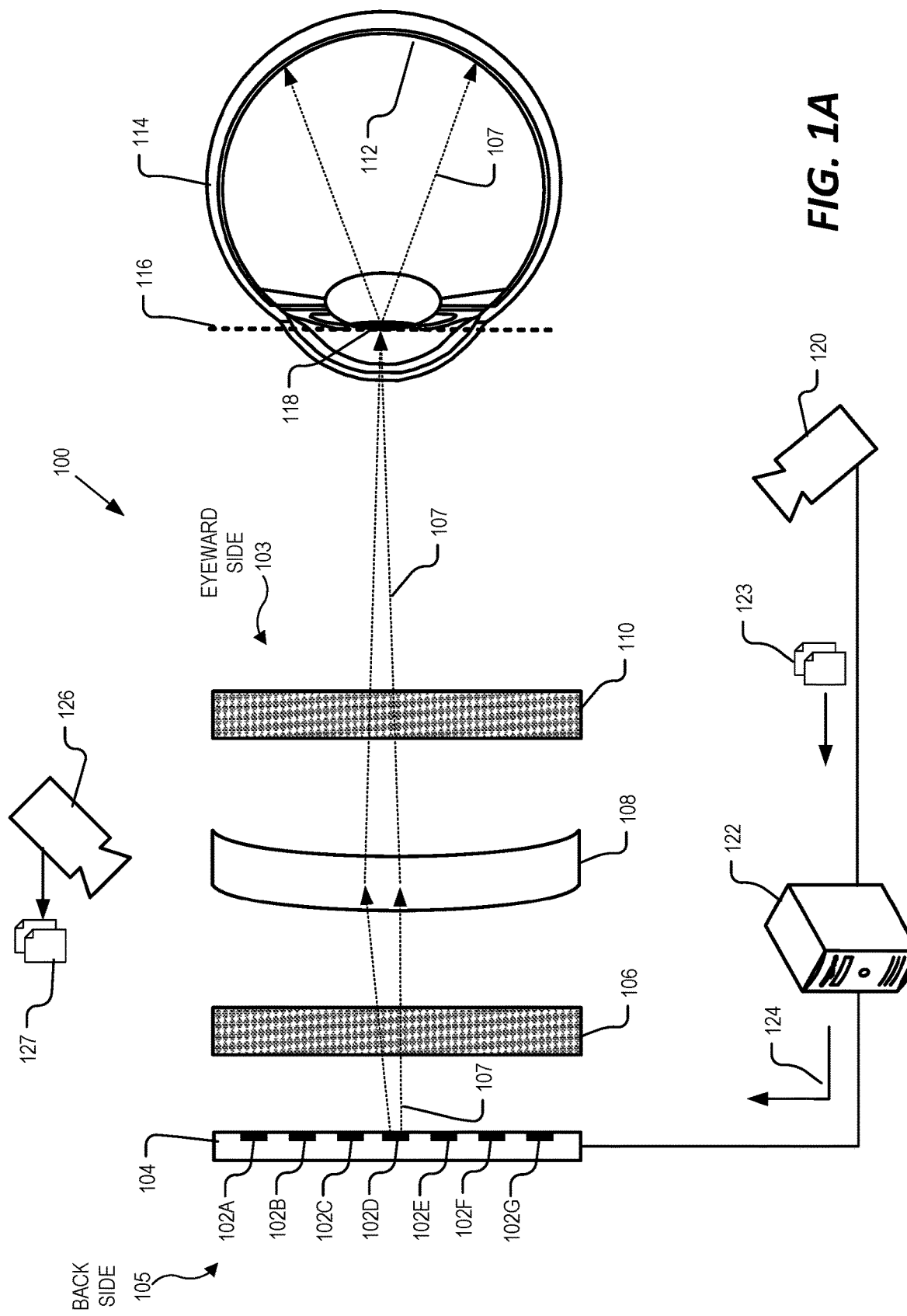
FIGS. 1A and 1B illustrate a fundus imaging system, in accordance with aspects of the present disclosure.

Various aspects and embodiments are disclosed in the following description and related drawings to show specific examples relating to a fundus imaging system that includes eye-tracking. Alternate aspects and embodiments will be apparent to those skilled in the pertinent art upon reading this disclosure and may be constructed and practiced without departing from the scope or spirit of the disclosure. Additionally, well-known elements will not be described in detail or may be omitted so as to not obscure the relevant details of the aspects and embodiments disclosed herein.

In some implementations of the disclosure, the term "near-eye" may be defined as including an element that is configured to be placed within 50 mm of an eye of a user while a near-eye device is being utilized. Therefore, a "near-eye optical element" or a "near-eye system" would include one or more elements configured to be placed within 50 mm of the eye of the user.

In aspects of this disclosure, visible light may be defined as having a wavelength range of approximately 380 nm-700 nm. Non-visible light may be defined as light having wavelengths that are outside the visible light range, such as ultraviolet light and infrared light. Infrared light having a wavelength range of approximately 700 nm-1 mm includes near-infrared light. In aspects of this disclosure, near-infrared light may be defined as having a wavelength range of approximately 700 nm-1.4 µm. White light may be defined as light that includes a broad range of wavelengths and in some instances may include multiple colors of the visible spectrum.

As mentioned above, the operation of some conventional fundus imaging systems may include directing a patient (or user) to fixate on a target image (e.g., a dot) that is projected onto their retina. One purpose of directing the patient to fixate on the target image is to ensure correct alignment between the eye and the illumination source (e.g. the flash) to maximize illumination of the fundus. However, in some instances, the patient may be unable to follow directions to fixate on the target due to a diminished capacity, either physical or developmental. For example, a user may have eye movement issues that prevents them from focusing on the target, or an infant/child may be unable to follow directions to focus on the target, and so on. If the eye is misaligned with the illumination source, the pupil of the eye may vignette the illumination light and prevent the light from reaching the fundus, which may degrade the resultant image.

Accordingly, aspects of the present disclosure provide a fundus imaging system that is invariant to eye movements and/or eye alignment. That is, a fundus imaging system may maintain illumination of the fundus even if the eye is not directly aligned with the illumination source and/or even as the eye moves. In one aspect, a fundus illumination source is provided that includes an array of light sources. An eye tracker may also be provided that tracks movements of the eye, where one or more of the light sources in the array are selectively enabled to emit illumination light based on the determined movements of the eye to maintain the illumination of the fundus while an image of the fundus is obtained. These and other features will be described in more detail below.

FIG. 1A illustrates a fundus imaging system 100, in accordance with aspects of the present disclosure. The fundus imaging system 100 is also shown as including an array of light sources 102A-102G, a layer 104, an optical combiner 106, a lens system 108, an optical combiner 110, a first camera 120, a computing device 122, and a second camera 126.

As shown in FIG. 1A, the light sources 102A-102G are disposed on layer 104. Layer 104 may be a transparent substrate, such as glass or plastic. In one example, the light sources 102A-102G may be encapsulated within the transparent substrate. The transparent substrate may be transmissive to visible light (e.g. 400 nm-750 nm) and may be configured to be placed on a display plane of an electronic or optical display layer (e.g., a liquid crystal display (LCD), an organic light emitting diode (OLED) display, a micro-LED display, a waveguide, etc.) that is configured to generate display light for presentation to the user. In another example, layer 104 is, itself, the electronic or optical display layer, where light sources 102A-102G are disposed on the display layer, interspersed within display light that is generated by the display layer (e.g., within the field of view of the user).

Each light source 102A-102G may be a micro light emitting diode (micro-LED), an edge emitting LED, a vertical cavity surface emitting laser (VCSEL) diode, or a Superluminescent diode (SLED). In addition, each light source 102A-102G may be individually enabled to emit non-visible light 107 to illuminate the eye 114. In some examples, non-visible light 107 is infrared light or near-infrared light. In some aspects, each light source 102A-102G is arranged on layer 104 in a two-dimensional (2D) array of columns and rows. In some examples, each light source 102A-102G may be referred to as a point light source, where only one of the light sources 102A-102G are enabled at a time to emit non-visible light 107 (e.g., in the illustrated example of FIG. 1A, only a single light source 102D is currently enabled to emit non-visible light 107).

In some examples, the array of light sources 102A-102G are positioned in a plane that is conjugate to a pupil plane 116 of the eye 114. In some implementations, the positioning of the array of light sources 102A-102G with respect to the eye 114 is obtained by way of a head/chinrest stand (not shown) that is provided to the user/patient. In other implementations, the positioning is provided by way of a head-mounted device (e.g., see head-mounted display of FIG. 5).

As shown in FIG. 1A, the lens system 108 is configured to receive the non-visible light 107 and direct the non-visible light 107 to illuminate the fundus 112 of the eye 114. In some examples, the lens system 108 provides a Maxwellian view where the lens system 108 converges the non-visible light 107 onto the pupil plane 116. As shown in FIG. 1A, the non-visible light 107 then expands as it passes through the pupil 118 towards to back of the eye 114 to illuminate a large area of the fundus 112. In some aspects, the lens system 108 includes a Fresnel lens. In other examples, the lens system 108 may include one or more other optical elements, such as a quarter waveplate and/or reflective polarizer. In some examples, the non-visible light 107 is generated by the light sources 102A-102G to have a particular polarization orientation. Thus, in some aspects, the lens system 108 may alter the polarization orientation of the non-visible light 107 as it propagates through the system.

FIG. 1A also illustrates fundus imaging system 100 as including an optical combiner 106 and an optical combiner 110. Optical combiner 106 is shown as being disposed between the array of light sources 102A-102G and the optical combiner 110. In particular, optical combiner 106 may be disposed between the array of light sources 102A-102G and the lens system 108. Optical combiner 110 is shown as being disposed between the array of light sources 102A-102G and the eyeward side 103 of the fundus imaging system 100, and in particular may be disposed between the lens system 108 and the eyeward side 103. As will be described in more detail below, the optical combiner 110 may be configured to direct reflected non-visible light (i.e., non-visible light that is reflected by the eye 114) to the first camera 120 to generate images 123 of the eye 114. Similarly, optical combiner 106 may be configured to direct reflected non-visible light to the second camera 126 to generate images 127 of the fundus 112.

In some aspects, the optical combiners 106 and 110 are transmissive to visible light (e.g. approximately 400 nm-700 nm), such as scene light (e.g., from the environment) that is incident on the backside 105 of the fundus imaging system 100. Even still, in some examples, optical combiners 106 and 110 are transmissive to visible light that generated by a display layer (e.g., layer 104). In some examples, optical combiner 106 and optical combiner 110 may each be configured as a respective polarization-selective volume hologram (a.k.a. polarized volume hologram (PVH)) that diffracts (in reflection) a particular polarization orientation of incident light having a particular wavelength toward cameras 126 and 120, respectively, while passing other polarization orientations/wavelengths.

When configured as a PVH, an optical combiner may include a plurality of liquid-crystal molecules spatially orientated to realize an optical function of the PVH. In some examples, a PVH may be configured to diffract light via Bragg diffraction. In some embodiments, the Bragg grating in the PVH may be generated by adding a chiral dopant to the liquid-crystals to induce a helical twist along a light propagation direction. The helix twist may be either left-handed or right-handed and, accordingly, the PVH may be referred to as a left-handed or a right-handed PVH. In some embodiments, the PVH may diffract circularly polarized light having a same handedness as the helix twist of the PVH and transmit circularly polarized light having an orthogonal handedness. That is, a left-handed PVH layer may diffract a left-handed circularly polarized ("LCP") light and transmit a right-handed circularly polarized ("RCP") light, while a right-handed PVH layer may diffract an RCP light and transmit an LCP light.

The angle between the incident light and the diffracted light may depend on the wavelength of the incident light and the Bragg period of the Bragg grating in the PVH. In some embodiments, depending on the alignment of the liquid-crystal molecules in the PVH, the PVH may further converge or diverge the incident light. In some examples, the PVH of the optical combiner may be also referred to as, a "polarization sensitive grating," a "polarization sensitive optical element," a "liquid crystal grating," or a "chiral liquid crystal element." When configured as a PVH, the optical combiners 106 and 110 may include flat or curved surfaces.

In some embodiments, optical combiner 106 may alternatively be configured as a "hot mirror". When configured as a hot mirror, the optical combiner 106 may include one or more reflecting layers that reflect non-visible light (e.g., having the same wavelength as the non-visible light 107) to the second camera 126 while passing visible light. The one or more hot mirrors may be in a line of sight of the user, but since the hot mirrors pass visible light, external scene light and/or display light will still propagate to the eye of the user. Therefore, in augmented reality (AR) implementations, a view of the external environment of the user is still viewable and in a virtual reality (VR) implementation, the user may view display light from a virtual reality display. In some examples, the hot mirror of optical combiner 106 may include a dichroic multi-layer optical film configured to reflect non-visible light of a particular spectrum and to pass other wavelengths of light, including visible light.

Figure 1B:
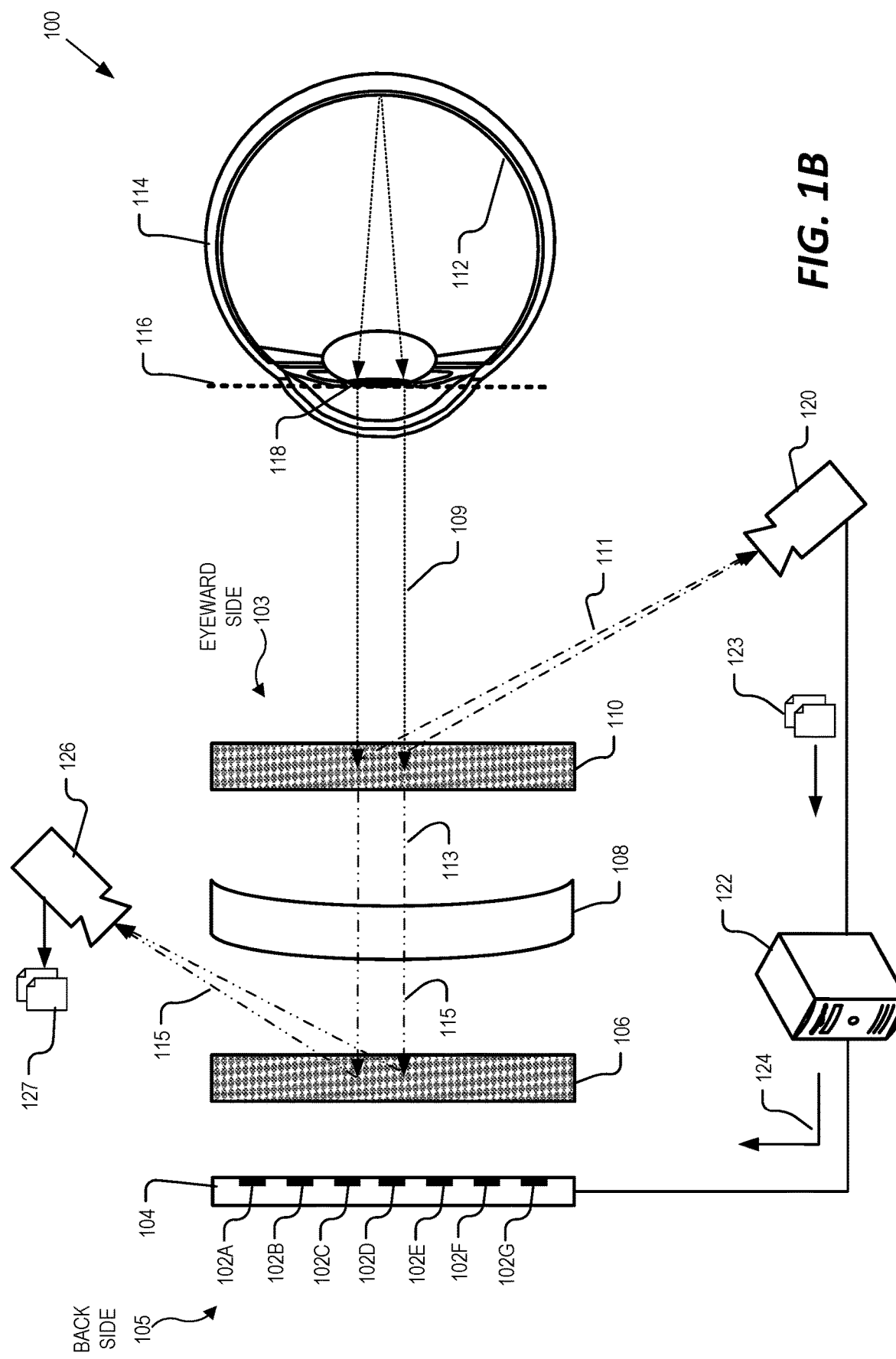

FIG. 1B illustrates an imaging optical path of the fundus imaging system 100 for generating images of the eye 114 and of the fundus 112, in accordance with aspects of the present disclosure. In some aspects, when illuminated with non-visible light 107, each point on the fundus 112 of eye 114 may operate as a point light source that reflects the non-visible light 107 as reflected non-visible light 109. Furthermore, the reflected non-visible light 109 may exit the eye 114 nearly collimated and as including multiple components (e.g., multiple polarization orientations). In some examples, one component of the reflected non-visible light 109 is a polarization orientation that is the same as the non-visible light 107 that was incident upon the fundus 112.

Figure 2A:
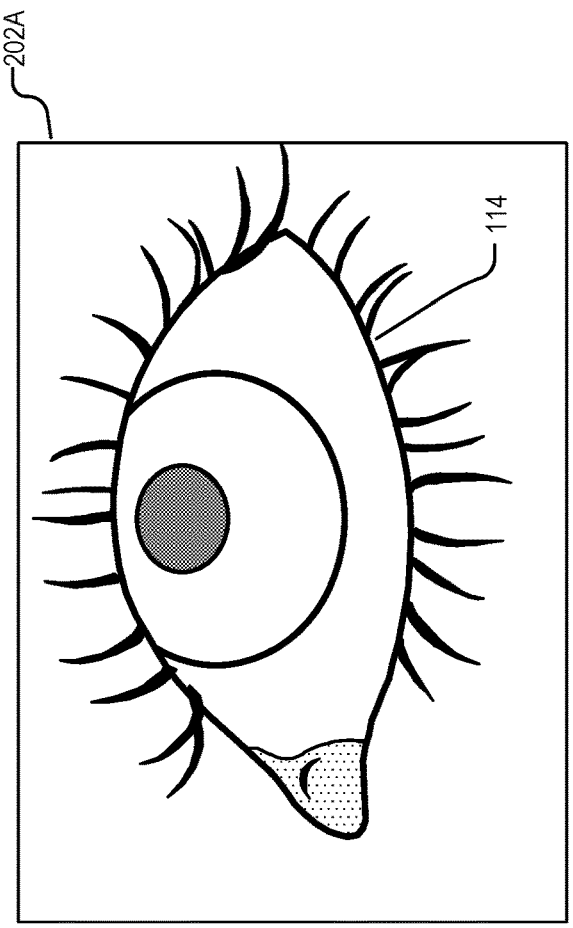
FIG. 2A illustrates an example image of an eye captured by a first camera for eye-tracking, in accordance with aspects of the present disclosure.

As shown in FIG. 1B, the reflected non-visible light 109 is received at the optical combiner 110. The optical combiner 110 may then direct a first component 111 of the reflected non-visible light to the first camera 120, where the first camera 120 then generates one or images 123 of the eye 114. FIG. 2A illustrates an example image 202A that may be captured by first camera 120. In some examples, first camera 120 may be configured to filter out light that is other than the non-visible light 107/reflected non-visible light 109 such that the first camera 120 only images the wavelength of the reflected non-visible light 109.

FIG. 1B further illustrates the optical combiner 110 passing the second component 113 of the reflected non-visible light 109. In some examples, the first component 111 of the reflected non-visible light 109 is a first polarization orientation (e.g., RCP), whereas the second component 113 is a second polarization orientation (e.g., LCP) that is orthogonal to the first polarization orientation.

Figure 2B:
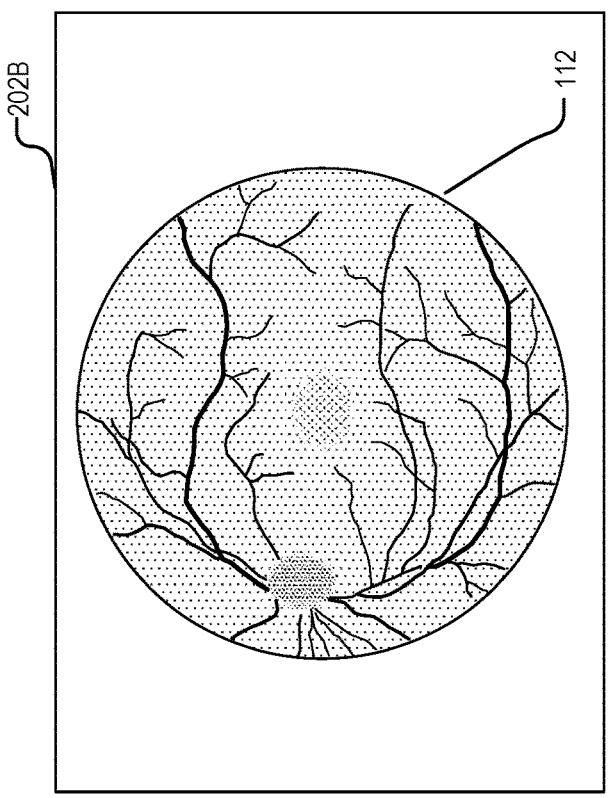
FIG. 2B illustrates an example image of a fundus, captured by a second camera, in accordance with aspects of the present disclosure.

The second component 113 of the reflected non-visible light 109 then passes through the lens system 108, which then transmits a fundus imaging light 115 that is responsive to the second component 113. For example, in some aspects the lens system 108 may alter the polarization orientation of the second component 113 of reflected non-visible light into a different polarization orientation and transmit the altered second component as fundus imaging light 115. In yet another example, the lens system 108 may maintain the polarization state of the second component 113 as it propagates through the lens system as fundus imaging light 115. In either case, when optical combiner 106 is implemented as a PVH, the PVH may be configured to reflect light of a particular polarization orientation (and wavelength) that is the same as the fundus imaging light 115 received from the lens system 108. In some examples, the fundus imaging light 115 has the same wavelength as that of the reflected non-visible light 109. The optical combiner 106 receives and directs the fundus imaging light 115 to the second camera 126, where the second camera 126 then generates one or images 127 of the fundus 112. FIG. 2B illustrates an example image 202B that may be captured by second camera 126. In some examples, the second camera 126 may be configured to filter out light that is other than the reflected non-visible light 109 such that the second camera 126 only images the wavelength of the reflected non-visible light 109.

In some examples, the fundus imaging system 100 may include an eye-tracking system to track movements of the eye 114. In the illustrated example, the eye-tracking system is provided by way of the first camera 120. The first camera 120 is communicatively coupled to computing device 122, which is configured to track movements of the eye 114 based on the one or more images 123. In some examples, the eye-tracking system is a pupil-tracker that is configured to determine the movements of the eye based on movements of the pupil 118.

In some examples, an eye-tracking module of the computing device 122 may be configured to determine eye-tracking information (e.g., location, orientation, gaze angle, etc. of the eye 114). In some aspects, the eye-tracking module may be configured to receive an image 123 captured by the first camera 120 and process the image to detect one or more specular reflections. The eye-tracking module may then localize the detected specular reflections to determine eye-tracking information (e.g., position, orientation, gaze angle, etc. of the eye 114). For example, the eye-tracking module may determine whether the eye 114 is looking in the straight, left, right, upwards, or downwards direction.

In some embodiments, the computing device 122 may include a control module that is communicatively coupled to the array of light sources 102A-102G. As shown in FIG. 1A, the eye 114 is generally looking forward and is aligned with a center of the array of light sources 102A-102G. Thus, in this scenario a center light source (e.g., light source 102D) may be enabled to emit the non-visible light 107. However, as mentioned above, if the eye 114 is not directly aligned, or if the eye 114 moves, the pupil 118 may vignette the non-visible light 107. Accordingly, the control module of computing device 122 may generate one or more control signals 124 to selectively enable at least one of the light sources 102A-102G based on the detected movements of the eye 114 to maintain illumination of the fundus 112.

For example, in some aspects, each light source 102A-102G of the array of light sources may include a corresponding position within the array. The control module may be configured to translate the detected movements of the eye 114 to a position within the array to determine which of the light sources 102A-102G to enable. In some embodiments, changing which of the light sources 102A-102G is enabled changes an angle at which the non-visible light 107 is emitted from the lens system 108. Thus, in operation, the eye-tracking module of computing device 122 may detect a movement of eye 114 based on one or more of the images 123, where the control module then translates the detected movements of the eye to a position of a light source in the array of light sources.

Figure 3:
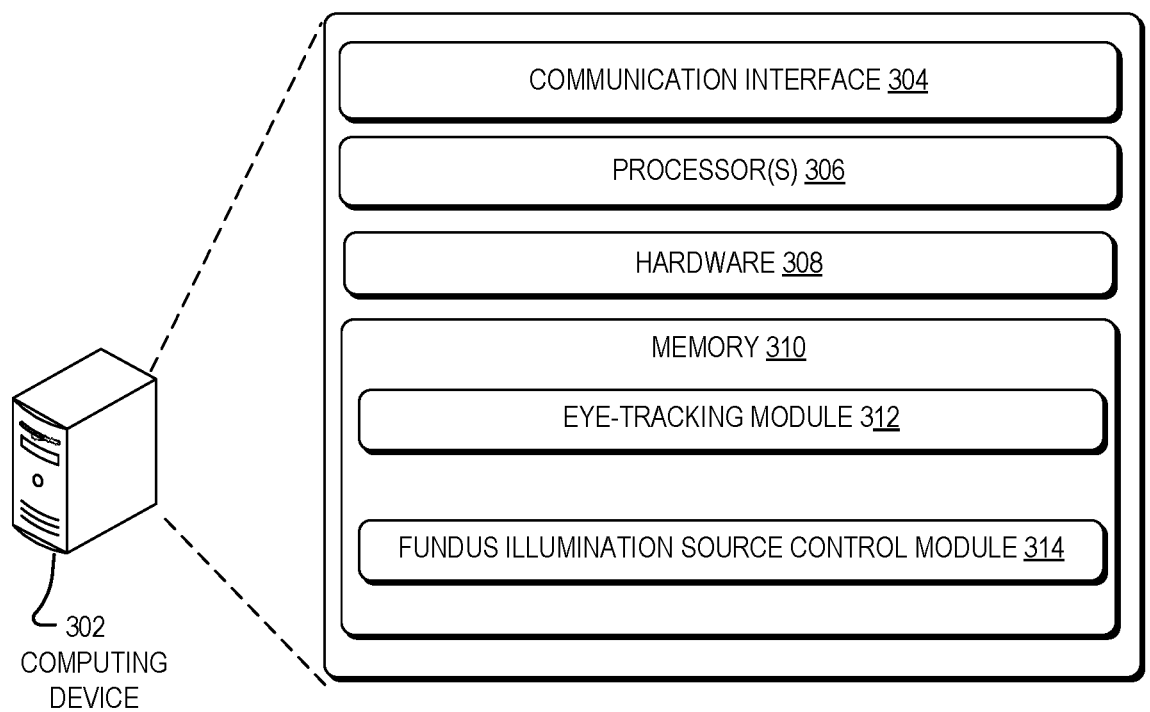
FIG. 3 illustrates a computing device, in accordance with aspects of the present disclosure.

FIG. 3 illustrates a computing device 302, in accordance with aspects of the present disclosure. The illustrated example of computing device 302 is shown as including a communication interface 304, one or more processors 306, hardware 308, and a memory 310. The computing device 302 of FIG. 3 is one possible implementation of the computing device 122 of FIG. 1A.

The communication interface 304 may include wireless and/or wired communication components that enable the computing device 302 to transmit data to and receive data from other devices/components. The hardware 308 may include additional hardware interface, data communication, or data storage hardware. For example, the hardware interfaces may include a data output device, and one or more data input devices.

The memory 310 may be implemented using computer-readable media, such as computer storage media. In some aspects, computer-readable media may include volatile and/or non-volatile, removable and/or non-removable media implemented in any method or technology for storage of information such as computer-readable instructions, data structures, program modules, or other data. Computer-readable media includes, but is not limited to, RAM, ROM, EEPROM, flash memory or other memory technology, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

The processors 306 and the memory 310 of the computing device 302 may implement an eye-tracking module 312 and a fundus illumination source control module 314. The eye-tracking module 312 and the fundus illumination source control module 314 may include routines, program instructions, objects, and/or data structures that perform particular tasks or implement particular abstract data types. The memory 310 may also include a data store (not shown) that is used by the eye-tracking module 312 and/or fundus illumination source control module 314.

The eye-tracking module 312 may be configured to receive images (e.g., images 123 of FIG. 1B) and process the images to determine a position and/or movements of the eye 114. The eye-tracking module 312 may then communicate with the fundus illumination source control module 314 based on the determined movements/position. The fundus illumination source control module 314 may be configured to translate the eye movements to a position within the array of light sources 102A-102G and generate one or more control signals (e.g., control signals 124) to enable at least one of the light sources 102A-102G to maintain illumination of the fundus 112.

Figure 4:
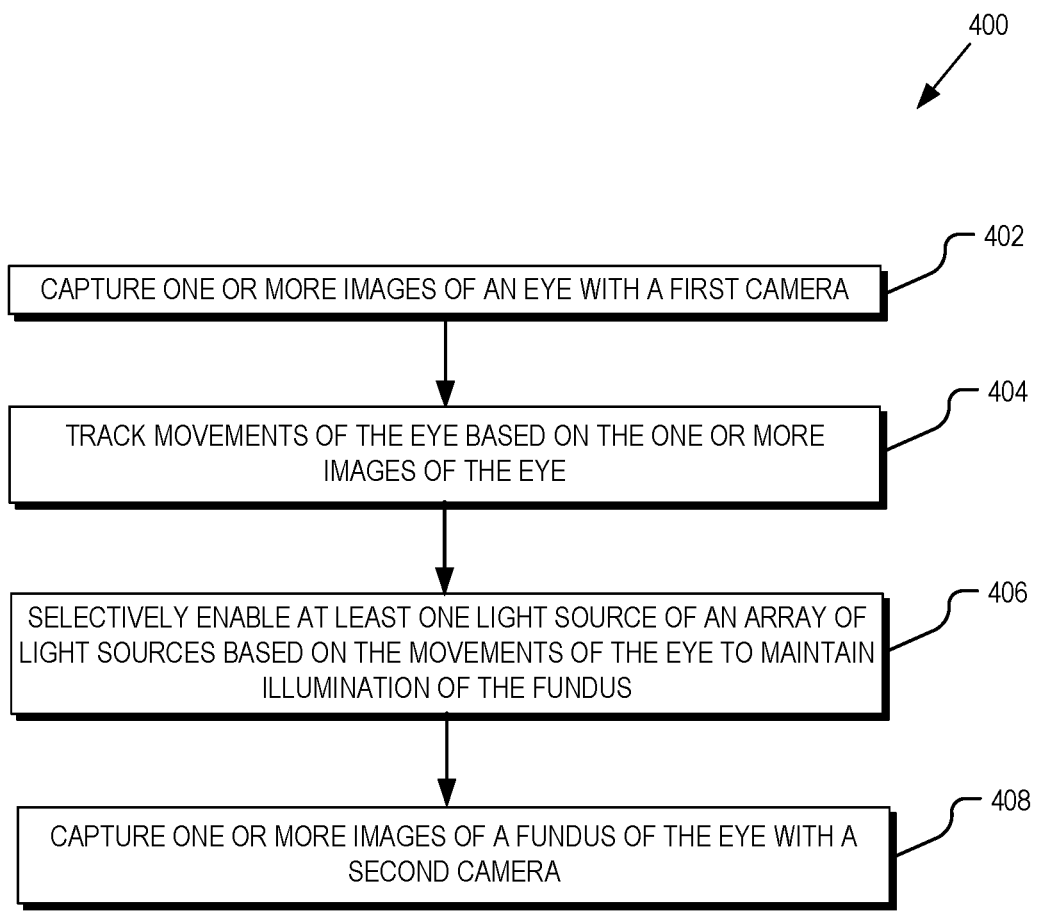
FIG. 4 is a flow chart illustrating a process of imaging the fundus of an eye, in accordance with aspects of the present disclosure.

FIG. 4 is a flow chart illustrating a process 400 of imaging the fundus of an eye, in accordance with aspects of the present disclosure. Process 400 includes one or more process blocks that may be performed by the computing device 122 of FIG. 1A and/or the computing device 302 of FIG. 3.

Process block 402 includes capturing one or more images (e.g., images 123 of FIG. 1B) of an eye (e.g., eye 114) with a first camera 120. In a process block 404, movements of the eye 114 are tracked. As discussed above, the computing device 122 may analyzes the images 123 to determine the position and/or movements of the eye 114. Next in a process block 406, the computing device 122 selectively enables at least one light source of the array of light sources 102A-102G based on the movements of the eye. As discussed above, the enabling of a light source may include translating the movements of the eye 114 to a position within the array of light sources to maintain illumination of the fundus 112 with non-visible light 107. Next, in process block 408, the second camera 126 may capture one or more images of the fundus 112.

In some implementations, aspects of the present disclosure, such as fundus imaging system 100 of FIG. 1A, may be utilized in a head mounted device, such as a virtual reality (VR) or augmented reality (AR) device. In some aspects, a head mounted device may incorporate an eye-tracking system to enhance a user's viewing experience. Eye-tracking, may in some instances, be aided by determining the position and/or movement of one or more features present in the fundus of the eye. For example, a head mounted device may be configured to identify a fovea region from an image of the fundus and then determine a gaze angle of the eye based on the identified fovea region. The fovea region may be determined using one or more image processing techniques. When the gaze angle is determined, a virtual image presented to a user by a display of a head mounted device may be adjusted in response to the determined gaze angle.

Figure 5:
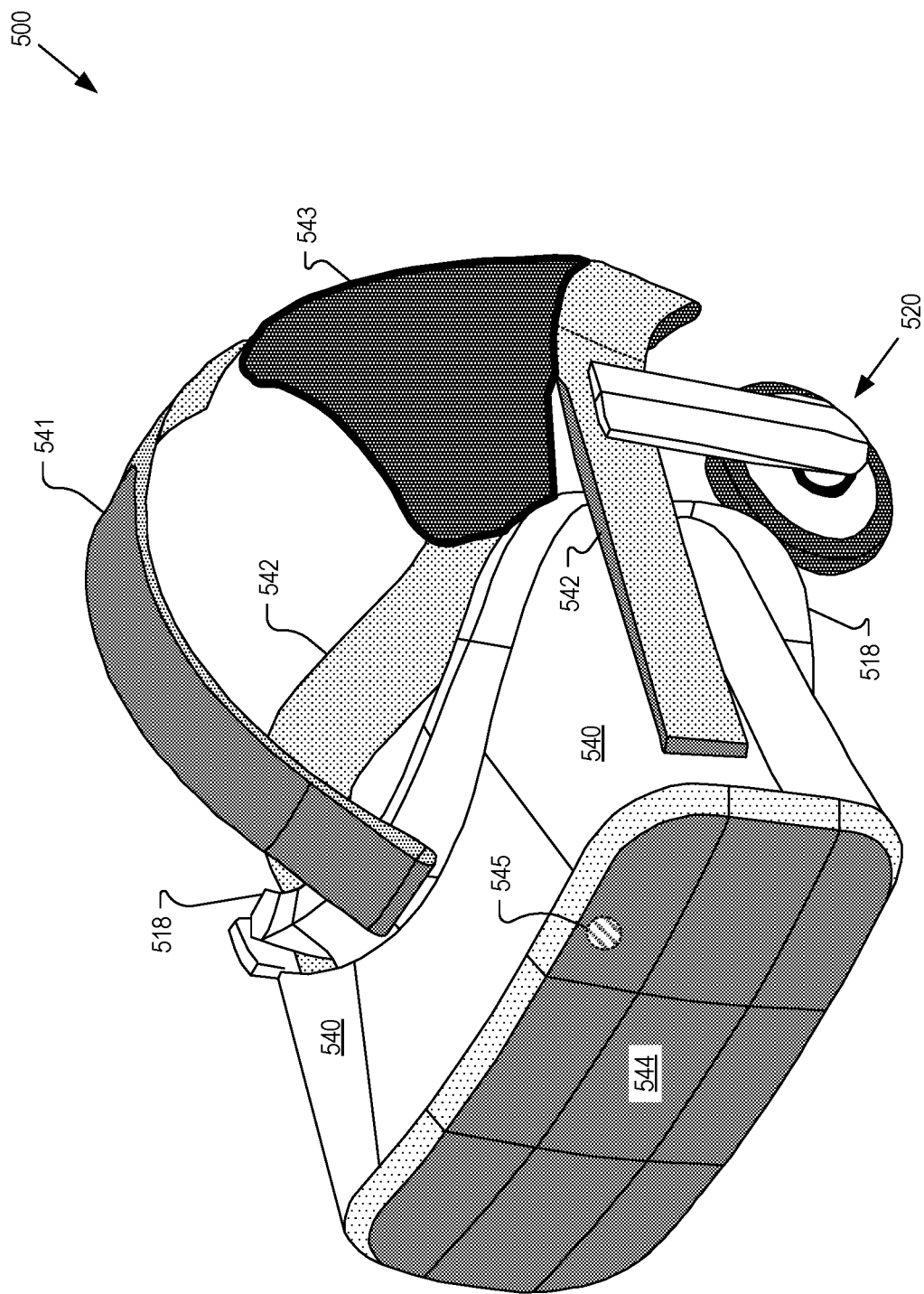
FIG. 5 illustrates a head mounted display (HMD), in accordance with aspects of the present disclosure.

By way of example, FIG. 5 illustrates a head-mounted display (HMD) 500, in accordance with aspects of the present disclosure. An HMD, such as HMD 500, is one type of head mounted device, typically worn on the head of a user to provide artificial reality content to a user. Artificial reality is a form of reality that has been adjusted in some manner before presentation to the user, which may include, e.g., virtual reality (VR), augmented reality (AR), mixed reality (MR), hybrid reality, or some combination and/or derivative thereof. The illustrated example of HMD 500 is shown as including a viewing structure 540, a top securing structure 541, a side securing structure 542, a rear securing structure 543, and a front rigid body 544. In some examples, the HMD 500 is configured to be worn on a head of a user of the HMD 500, where the top securing structure 541, side securing structure 542, and/or rear securing structure 543 may include a fabric strap including elastic as well as one or more rigid structures (e.g., plastic) for securing the HMD 500 to the head of the user. HMD 500 may also optionally include one or more earpieces 520 for delivering audio to the ear(s) of the user of the HMD 500.

The illustrated example of HMD 500 also includes an interface membrane 518 for contacting a face of the user of the HMD 500, where the interface membrane 518 functions to block out at least some ambient light from reaching to the eyes of the user of the HMD 500.

Example HMD 500 may also include a chassis for supporting hardware of the viewing structure 540 of HMD 500 (chassis and hardware not explicitly illustrated in FIG. 5). The hardware of viewing structure 540 may include any of processing logic, wired and/or wireless data interface for sending and receiving data, graphic processors, and one or more memories for storing data and computer-executable instructions. In one example, viewing structure 540 may be configured to receive wired power and/or may be configured to be powered by one or more batteries. In addition, viewing structure 540 may be configured to receive wired and/or wireless data including video data.

Viewing structure 540 may include a display system having one or more electronic displays for directing light to the eye(s) of a user of HMD 500. The display system may include one or more of a liquid crystal display (LCD), an organic light emitting diode (OLED) display, a micro-LED display, etc. for emitting light (e.g., content, images, video, etc.) to a user of HMD 500. The viewing structure 540 may also include an optical assembly that is configured to receive the image light from the display system and generate a virtual image (e.g., by collimating the image light) for viewing by an eye of a wearer of the HMD 500.

In some examples, viewing structure includes a fundus imaging system 545 for obtaining one or more images of a fundus of the user's eye. The fundus imaging system 545 may be implemented by way of any of the embodiments discussed herein, including fundus imaging system 100 of FIG. 1A.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A fundus imaging system, comprising:
    an array of light sources configured to be selectively enabled to emit non-visible light to illuminate a fundus of an eye;
    a first optical combiner disposed between the array of light sources and an eyeward side of the fundus imaging system, wherein the first optical combiner is configured to:
        receive reflected non-visible light that is reflected by the eye,
        direct a first component of the reflected non-visible light to a first camera to generate an image of the eye, and
        pass a second component of the reflected non-visible light through the first optical combiner towards the array of light sources; and
    a second optical combiner disposed between the array of light sources and the first optical combiner, wherein the second optical combiner is configured to:
        receive a fundus imaging light responsive to the second component of the reflected non-visible light, and
        direct the fundus imaging light to a second camera to generate an image of the fundus.

2. The fundus imaging system of claim 1, further comprising:
    a computing device configured to determine movements of the eye based on the image of the eye and to selectively enable at least one light source of the array of light sources based on the movements to maintain illumination of the fundus.

3. The fundus imaging system of claim 1, wherein the non-visible light comprises infrared or near-infrared light.

4. The fundus imaging system of claim 1, further comprising:
    a lens system disposed between the first optical combiner and the second optical combiner, wherein the lens system is configured to direct the non-visible light emitted by at least one light source of the array of light sources to illuminate the fundus of the eye.

5. The fundus imaging system of claim 4, wherein the lens system is configured to focus the non-visible light to a pupil plane of the eye.

6. The fundus imaging system of claim 1, wherein the first component of the reflected non-visible light is a first polarization orientation, and wherein the second component of the reflected non-visible light is a second polarization orientation that is orthogonal to the first polarization orientation.

7. The fundus imaging system of claim 6, wherein the first optical combiner comprises a first polarized volume hologram configured to direct the reflected non-visible light of the first polarization orientation and to pass the reflected non-visible light of the second polarization orientation.

8. The fundus imaging system of claim 1, wherein the second optical combiner is configured to direct light to the second camera based on a wavelength of the fundus imaging light having a same wavelength as the non-visible light.

9. The fundus imaging system of claim 8, wherein the second optical combiner comprises a second polarized volume hologram configured to direct the fundus imaging light to the second camera based on a polarization orientation and the wavelength of the fundus imaging light.

10. The fundus imaging system of claim 8, wherein the second optical combiner comprises a hot mirror that is configured to direct the fundus imaging light to the second camera based on the wavelength of the fundus imaging light.

11. The fundus imaging system of claim 1, wherein the array of light sources comprises a transparent substrate and wherein each light source of the array of light sources is disposed on the transparent substrate.

12. The fundus imaging system of claim 1, wherein the first optical combiner and the second optical combiner are transmissive to visible light.

13. A fundus imaging system, comprising:
    a first camera configured to generate at least one image of an eye;
    a second camera configured to generate at least one image of a fundus of the eye;
    an array of light sources configured to be selectively enabled to emit non-visible light to illuminate a fundus of an eye;
    a first optical combiner disposed between the array of light sources and an eyeward side of the fundus imaging system, wherein the first optical combiner is configured to:
        receive reflected non-visible light that is reflected by the eye,
        direct a first component of the reflected non-visible light to the first camera to generate the at least one image of the eye, and
        pass a second component of the reflected non-visible light through the first optical combiner towards the array of light sources; and
    a second optical combiner disposed between the array of light sources and the first optical combiner, wherein the second optical combiner is configured to:
        receive a fundus imaging light responsive to the second component of the reflected non-visible light, and
        direct the fundus imaging light to the second camera to generate the at least one image of the fundus.

14. The fundus imaging system of claim 1, wherein the first component comprises a first polarization orientation or a first wavelength of the reflected non-visible light and wherein the second component comprises a second polarization orientation or a second wavelength of the reflected non-visible light.

15. The fundus imaging system of claim 1, wherein the array of light sources are configured to be positioned in a plane that is conjugate to a pupil plane of the eye.

16. The fundus imaging system of claim 4, wherein the lens system is configured to converge the non-visible light onto a pupil plane of the eye.

17. The fundus imaging system of claim 13, wherein the first component comprises a first polarization orientation or a first wavelength of the reflected non-visible light and wherein the second component comprises a second polarization orientation or a second wavelength of the reflected non-visible light.

18. The fundus imaging system of claim 13, wherein the array of light sources are configured to be positioned in a plane that is conjugate to a pupil plane of the eye.

19. The fundus imaging system of claim 18, further comprising:
   a lens system disposed between the first optical combiner and the second optical combiner, wherein the lens system is configured to converge the non-visible light emitted by at least one light source of the array of light sources onto the pupil plane of the eye.

* * * * *